(12) United States Patent
Jacquin et al.

(10) Patent No.: US 8,364,254 B2
(45) Date of Patent: Jan. 29, 2013

(54) METHOD AND DEVICE FOR PROBABILISTIC OBJECTIVE ASSESSMENT OF BRAIN FUNCTION

(75) Inventors: Arnaud Jacquin, New York, NY (US); Elvir Causevic, Manchester, MO (US)

(73) Assignee: Brainscope Company, Inc., Bethesda, MD (US)

( * ) Notice: Subject to any disclaimer, the term of this patent is extended or adjusted under 35 U.S.C. 154(b) by 520 days.

(21) Appl. No.: 12/361,174

(22) Filed: Jan. 28, 2009

(65) Prior Publication Data

US 2010/0191139 A1 Jul. 29, 2010

(51) Int. Cl.
*A61B 5/00* (2006.01)
(52) U.S. Cl. .................................................... 600/544
(58) Field of Classification Search .................. 600/544
See application file for complete search history.

(56) References Cited

U.S. PATENT DOCUMENTS

| | | | |
|---|---|---|---|
| 4,188,956 A | 2/1980 | John | |
| 4,421,122 A * | 12/1983 | Duffy | 600/544 |
| 4,913,160 A | 4/1990 | John | |
| 6,360,122 B1 | 3/2002 | Fischell et al. | |
| 6,625,485 B2 * | 9/2003 | Levendowski et al. | 600/544 |
| 6,654,623 B1 | 11/2003 | Kästle | |
| 6,757,558 B2 | 6/2004 | Lange et al. | |
| 6,804,661 B2 * | 10/2004 | Cook | 706/20 |
| 6,947,790 B2 * | 9/2005 | Gevins et al. | 600/544 |
| 7,054,453 B2 | 5/2006 | Causevic et al. | |
| 7,089,927 B2 | 8/2006 | John et al. | |
| 7,299,088 B1 | 11/2007 | Thakor et al. | |
| 7,302,064 B2 | 11/2007 | Causevic et al. | |
| 7,373,198 B2 | 5/2008 | Bibian et al. | |
| 7,647,098 B2 | 1/2010 | Prichep | |
| 2002/0039455 A1 | 4/2002 | Kanamaru et al. | |
| 2004/0210124 A1 | 10/2004 | Nowinski et al. | |
| 2005/0070458 A1 | 3/2005 | John | |
| 2005/0165323 A1 | 7/2005 | Montgomery | |
| 2005/0165327 A1 | 7/2005 | Thibault et al. | |
| 2006/0004753 A1 | 1/2006 | Coifman et al. | |
| 2006/0155751 A1 | 7/2006 | Geshwind et al. | |
| 2006/0217632 A1 | 9/2006 | Causevic et al. | |
| 2007/0032737 A1 | 2/2007 | Causevic et al. | |

(Continued)

FOREIGN PATENT DOCUMENTS

EP 1 275 340 A1 1/2003
WO WO 91/09372 A1 6/1991

(Continued)

OTHER PUBLICATIONS

U.S. Appl. No. 12/105,439, filed Apr. 18, 2008.

(Continued)

*Primary Examiner* — Max Hindenburg
(74) *Attorney, Agent, or Firm* — Finnegan, Henderson, Farabow, Garrett & Dunner LLP

(57) ABSTRACT

A method and apparatus for providing objective assessment of the brain state of a subject using a field portable device. The method includes placing an electrode set coupled to a handheld base unit on the subject's head, acquiring electrical brain signals from the subject through the electrode set, processing the acquired electrical brain signals using a feature extraction algorithm, classifying the extracted features into brain states, computing brain abnormality indices reflecting the probability of correct classification of brain state, and graphically displaying the classification result and the abnormality indices on the handheld base unit.

32 Claims, 9 Drawing Sheets

U.S. PATENT DOCUMENTS

| | | | |
|---|---|---|---|
| 2007/0100251 | A1 | 5/2007 | Prichep |
| 2007/0173732 | A1 | 7/2007 | Causevic et al. |
| 2008/0208073 | A1 | 8/2008 | Causevic |
| 2008/0208074 | A1* | 8/2008 | Snyder et al. ............ 600/545 |
| 2008/0249430 | A1 | 10/2008 | John et al. |
| 2008/0262371 | A1 | 10/2008 | Causevic |
| 2009/0018427 | A1 | 1/2009 | Causevic et al. |
| 2009/0082690 | A1 | 3/2009 | Phillips |
| 2009/0221930 | A1 | 9/2009 | Laken |
| 2009/0247894 | A1 | 10/2009 | Causevic |
| 2009/0263034 | A1 | 10/2009 | Causevic |
| 2009/0264785 | A1 | 10/2009 | Causevic et al. |
| 2009/0264786 | A1 | 10/2009 | Jacquin |
| 2010/0041962 | A1 | 2/2010 | Causevic et al. |

FOREIGN PATENT DOCUMENTS

| | | |
|---|---|---|
| WO | WO 2006/034024 | 3/2006 |
| WO | WO 2007/016149 A2 | 2/2007 |
| WO | WO 2007/096452 | 8/2007 |
| WO | WO 2009/063463 A2 | 5/2009 |
| WO | WO 2010/088252 A1 | 8/2010 |

OTHER PUBLICATIONS

U.S. Appl. No. 12/106,699, filed Apr. 21, 2008.
PCT International Search Report and the Written Opinion mailed Apr. 8, 2010, in related PCT Application No. PCT/US2010/022197.
Besserve et al., "Classification methods for ongoing EEG and MEG signals", Bio Res, vol. 40 , No. 4, 2007, pp. 415-437.
Blakely, "A fast empirical mode decomposition technique for nonstationary nonlinear time series", Center for Scientific Computation and Mathematical Modeling, University of Maryland, College Park, Oct. 3, 2005.
Coifman et al., "Geometric diffusions as a tool for harmonic analysis and structure definition of data: Multiscale methods," Proceedings of the National Academy of Sciences (PNAS), vol. 102, No. 21, May 24, 2005, pp. 7432-7437.
Coifman et al., "Multiresolution analysis associated to diffusion semigroups: construction and fast algorithms," Tech. Rep. YALE/DCS/TR-1292, Dept. Comp. Sci., Yale University, Jun. 2004, pp. 1-32.
Comon, "Independent component analysis, a new concept?," Signal Processing, 36:287-314 (1994).
Copending U.S. Appl. No. 12/541,272, filed Aug. 14, 2009.
Copending U.S. Appl. No. 12/576,521, filed Oct. 9, 2009.
Copending U.S. Appl. No. 12/639,357, filed Dec. 16, 2009.
Delorme et al., "Enhanced detection of artifacts in EEG data using higher-order statistics and independent component analysis," NeuroImage 34:1443-1449 (2007).
Hadjileontiadis et al., "Empirical mode decomposition and fractal dimension filter," IEEE Engineering in Medicine and Biology Magazine, Jan./Feb. 2007, p. 30-39.
Higuchi, "Approach to an irregular time series on the basis of the fractal theory," Physica D 31:277-283 (1988).
Hyvarinen, "Fast and robust fixed-point algorithms for independent component analysis," IEEE Transactions on Neural Networks 10(3):626-634 (1999).
John, "Principles of neurometrics", American Journal of EEG Technology, American Society of EEG Technologists, vol. 30, No. 4, Dec. 1, 1990, pp. 251-266.
Jung et al., "Removing electroencephalographic artifacts by blind source separation," Psychophysiology, vol. 37, pp. 163-178, 2000.
Konstam, "Linear discriminant, analysis using genetic algorithms", Applied Computing: States of the Art and Practice—1993. Proceedings of the 1993 ACM/SGAPP Symposium on Applied Computing ACM New York, NY, 1993, pp. 152-156.
Ksiezyk et al., "Neural networks with wavelet preprocessing in EEG artifact recognition," Laboratory of Medical Physics, Institute of Experimental Physics, Warsaw University, Hoza 69 00 681 Warszawa, Poland.
Mahadevan et al., "Valvefunction approximation with diffusion wavelets and laplacian eigenfunctions," University of Massachusetts, Dept. of Computer Science TR-2005-38, and NIPS, accepted, 2005.
PCT International Search Report and Written Opinion issued by European Patent Office in International Application No. PCT/US2009/040604, mailing date Jul. 14, 2009.
PCT International Search Report and Written Opinion mailed Dec. 27, 2010, in related PCT/US2010/045290.
PCT International Search Report and Written Opinion mailed Dec. 28, 2010, in related PCT/US2010/051621.
PCT International Search Report and Written Opinion mailed Jun. 8, 2009, in related PCT/US2009/041109.
PCT International Search Report and Written Opinion mailed Mar. 14, 2011, in related PCT/US2010/060170.
Prusseit et al., "Stochastic Qualifiers of Epileptic Brain Function," Phys Rev Lett 98, 138103 (2007).
Vorobyov et al., "Blind noise reduction for multisensory signals using ICA and subspace filtering, with application to EEG analysis," Biol. Cybern. 86, 293-303 (2002).

* cited by examiner

BFI: BRAIN FOCALITY INDEX

BAI_SB: BRAIN ABNORMALITY INDEX FOR ABNORMAL BRAIN FUNCTION OF TYPE: "STROKE OR BLEED"

BAI_Alc: BRAIN ABNORMALITY INDEX FOR ABNORMAL BRAIN FUNCTION OF TYPE: "ALCOHOL"

BAI_Enc: BRAIN ABNORMALITY INDEX FOR ABNORMAL BRAIN FUNCTION OF TYPE: "ENCEPHALOPATHY"

BAI_Dep: BRAIN ABNORMALITY INDEX FOR ABNORMAL BRAIN FUNCTION OF TYPE: "UNIPOLAR, BIPOLAR DISORDER"

BAI_Dem: BRAIN ABNORMALITY INDEX FOR ABNORMAL BRAIN FUNCTION OF TYPE: "DEMENTIA"

BAI_TBI: BRAIN ABNORMALITY INDEX FOR ABNORMAL BRAIN FUNCTION OF TYPE: "TRAUMATIC BRAIN INJURY"

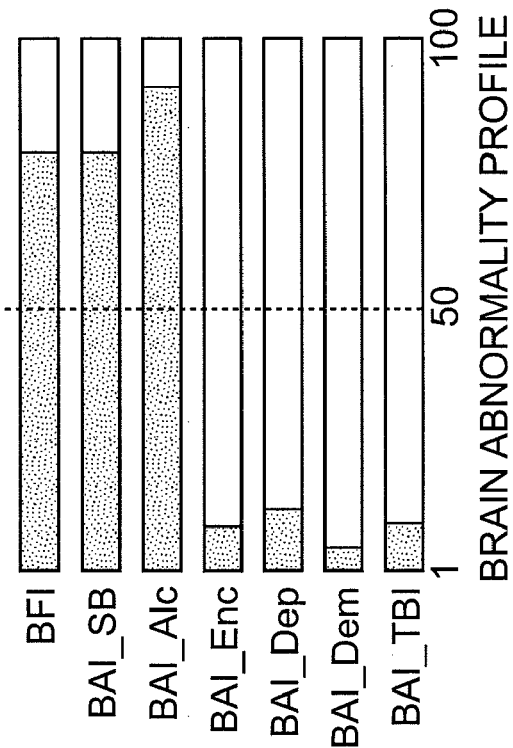

BRAIN ABNORMALITY PROFILE

FIG. 9

METHOD AND DEVICE FOR PROBABILISTIC OBJECTIVE ASSESSMENT OF BRAIN FUNCTION

TECHNICAL FIELD

The present invention relates to the field of neurological evaluation, and specifically, to a portable apparatus and method for objective assessment of brain function using numerical indices or maps indicative of brain abnormalities.

BACKGROUND

The brain performs the most complex and essential processes in the human body. Surprisingly, contemporary health care lacks sophisticated tools to objectively assess brain function at the point-of-care. A patient's mental and neurological status is typically assessed by an interview and a subjective physical exam. Clinical laboratories currently have no capacity to assess brain function or pathology, contributing little more than identification of poisons, toxins, or drugs that may have externally impacted the central nervous system (CNS).

Brain imaging studies, such as computed tomography (CT) and magnetic resonance imaging (MRI) are widely used to visualize the structure of the brain. However, CT scan and MRI are anatomical tests and reveal very little information about brain function. For example, intoxication, concussion, active seizure, metabolic encephalopathy, infections, and numerous other conditions (e.g. diabetic coma) show no abnormality on CT scan. A classical stroke, or a traumatic brain injury (TBI), may not be immediately visible in an imaging test even if there is a clear and noticeably abnormal brain function. Similarly, diffuse axonal injury (DAI), related to shearing of nerve fibers which is present in a majority of concussive brain injury cases, can remain invisible on most routine structural images. If undetected at an early stage, swelling or edema from DAI can subsequently lead to coma and death.

Functional MRI (fMRI) is a recent improvement over MRI, which provides relative images of the concentration of oxygenated hemoglobin in various parts of the brain. While the concentration of oxygenated hemoglobin is a useful indication of the metabolic function of specific brain regions, it provides very limited or no information about the underlying brain function, i.e., the processing of information by the brain, which is electrochemical in nature.

Further, CT and MRI/fMRI testing devices are not field-deployable due to their size, power requirements and cost. These assessment tools play an important role in selected cases, but they are not universally available, require experienced personnel to operate, and they do not provide critical information at the early stages of acute neurological conditions. Current technologies are unable to provide the immediate information critical to timely intervention, appropriate triage, or the formulation of an appropriate plan of care for acute brain trauma. Unfortunately, the brain has very limited capacity for repair, and thus time-sensitive triage and intervention is very important in treating brain injuries.

Currently, emergency room patients with altered mental status, acute neuropathy, or head trauma must undergo costly and time-consuming tests to determine an appropriate course of treatment. Unfortunately, in many cases, the clinical condition of patients continue to deteriorate as they wait for equipment to become available or for specialists to interpret tests. The problem that faces ER physicians is that their resources are limited to a subjective physical exam using a flashlight and a reflex hammer, and all of the physician's decisions concerning the administration of emergency treatment, additional consultation by a neurologist, or patient discharge, are based on the results of this simplistic exam. Often, ER patients are sent for imaging studies, yet many functional brain abnormalities, as discussed earlier, are not visible on a CT scan or MRI. Some abnormalities which eventually have anatomical and structural consequences often take time to become visible on an imaging test. This is true for many important conditions, such as ischemic stroke, concussion, raised intracranial pressure, and others. This indicates the need for real-time, functional brain state assessment technology, which can be performed in the ER, or in an ambulatory setting, and can detect emergency neurological conditions hours ahead of the standard clinical assessment tools available today.

All of the brain's activities, whether sensory, cognitive, emotional, autonomic, or motor function, is electrical in nature. Through a series of electrochemical reactions, mediated by molecules called neurotransmitters, electrical potentials are generated and transmitted throughout the brain, traveling continuously between and among the myriad of neurons. This activity establishes the basic electrical signatures of the electroencephalogram (EEG) and creates identifiable frequencies which have a basis in anatomic structure and function. Understanding these basic rhythms and their significance makes it possible to characterize the electrical brain signals as being within or beyond normal limits. At this basic level, the electrical signals serve as a signature for both normal and abnormal brain function. Just as an abnormal electrocardiogram (ECG) pattern is a strong indication of a particular heart pathology, an abnormal brain wave pattern is a strong indication of a particular brain pathology.

Even though EEG-based neurometric technology is accepted today in neurodiagnostics, its application in the clinical environment is notably limited. Some of the barriers limiting its adoption include: the cost of EEG equipment, the need for a skilled technician to administer the test, the time it takes to conduct the test, and the need for expert interpretation of the raw data. More importantly, the lack of portability of this technology makes it infeasible for point-of-care applications. A fully-equipped diagnostic EEG instrument typically costs around $80,000. Despite the high costs, the instrument produces essentially raw waveforms which must be carefully interpreted by an expert. Moreover, use of the standard EEG equipment remains extremely cumbersome. It can take 30 minutes or more to apply the required 19 electrodes. Once a subject is prepared for the test, the EEG recording can take from 1 to 4 hours. Data is collected and analyzed by an EEG technician, and is then presented to a neurologist for interpretation and clinical assessment. This makes the currently available EEG equipment inadequate for neuro-triage applications in emergency rooms or at other point-of-care settings. Thus, there is an immediate need for a portable brain state assessment technology to provide rapid neurological evaluation and treatment guidance for patients with acute brain injury or disease, so as to prevent further brain damage and disability. Additionally, there is a need for objective quantification of brain functionality in order to enable clinicians, EMTs or ER personnel, who are not well trained in neurodiagnostics, to easily interpret and draw diagnostic inferences from the recorded data. This in turn will help the medical personnel in selecting an immediate course of action, prioritizing patients for imaging, or determining if immediate referral to a neurologist or neurosurgeon is required.

SUMMARY

The present disclosure describes a method and apparatus for objective assessment of the brain state of a subject using electrical brain signals. A first aspect of the present disclosure includes a method of assessing brain state by recording electrical brain signals of the subjects using at least one electrode, extracting quantitative features from the recorded brain electrical signals, classifying the extracted features into brain states, and computing a probabilistic index of the accuracy of classification.

A second aspect of the present disclosure includes a portable brain state assessment device using Bx™ technology, which includes a headset comprising a plurality of brain-electrical-signal-detecting electrodes, and a handheld base unit operatively coupled to the headset, the base unit comprising a processor configured to extract quantitative features from the recorded signal, classify the extracted features into brain states, and compute probabilistic indices indicating the accuracy of the classification. The portable device further comprises a display unit to provide a visual display of the classified brain state and the probabilistic indices.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the various aspects of the invention.

BRIEF DESCRIPTION OF DRAWINGS

FIG. 9 illustrates a Brain Abnormality Profile for a subject suffering from multiple brain function disorders.

DETAILED DESCRIPTION

Reference will now be made in detail to embodiments consistent with the present disclosure, examples of which are illustrated in the accompanying drawings. Wherever possible, the same reference numbers will be used throughout the drawings to refer to the same or like parts.

In an exemplary embodiment, data corresponding to brain electrical activity is used to assess the brain function of a subject. The electrical brain signals are measured and analyzed at the point-of-care using a portable brain-state assessment device developed using Bx™ technology. In accordance with an exemplary embodiment of the Bx™ technology, a subject's electrical brain activity is recorded using a varying number of non-invasive electrodes located at standardized positions on the scalp and forehead, and the subject's brain electrical signals are assessed with reference to one or more databases. For example, collected normative data, indicative of normal brain electrical activity, is used to establish quantitative features which clearly distinguish brain signals produced in the presence and absence of brain disorders. This normative dataset includes brain activity data of a control group or population comprising of individuals similar to the subject in one or more aspects, such as age, gender, etc. The collected normative database employed by the inventor has been shown to be independent of racial background and to have extremely high test-retest reliability, specificity (low false positive rate) and sensitivity (low false negative rate).

Figure 1:
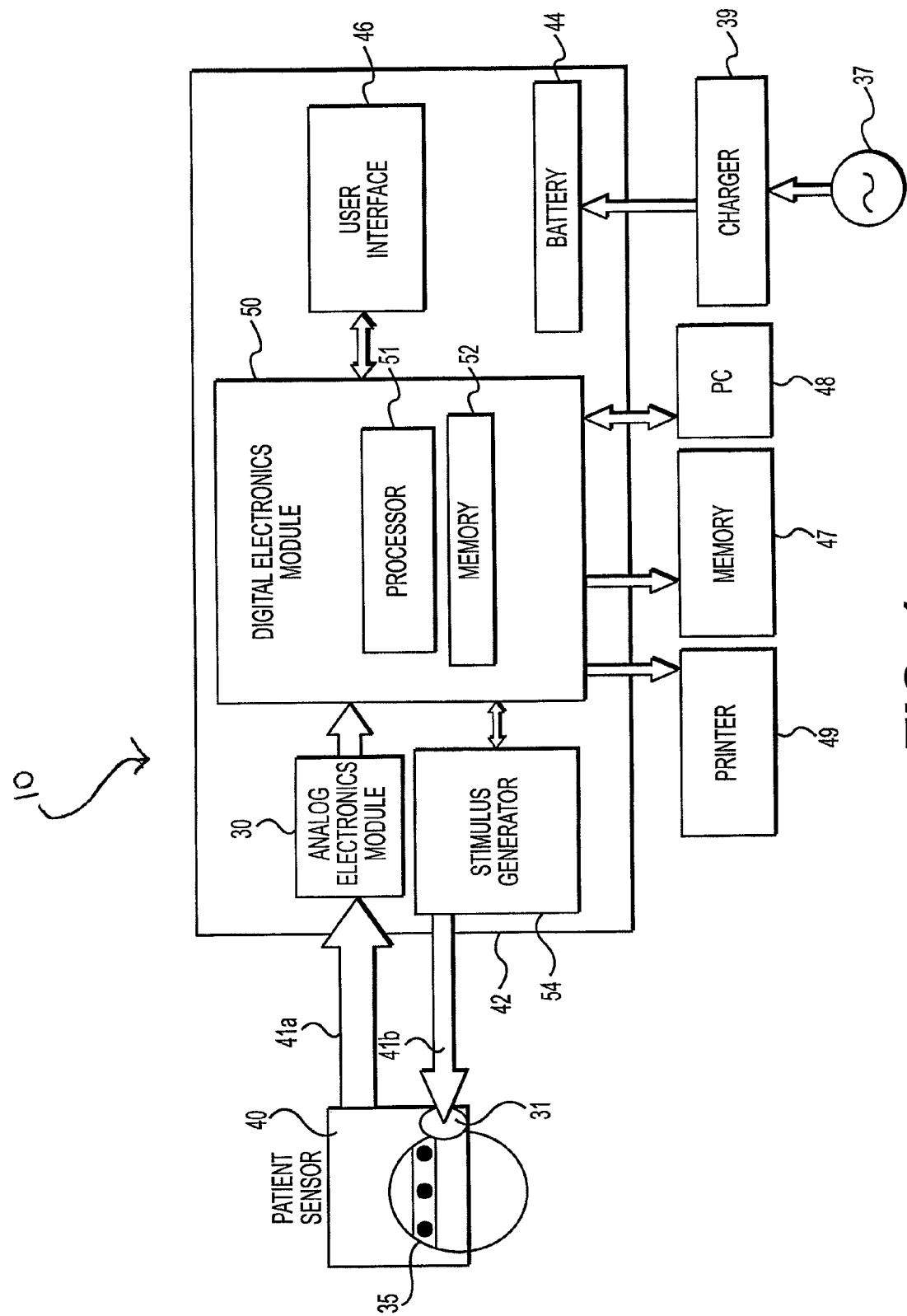
FIG. 1 illustrates a device for recording and processing electrical brain signals to assess the brain state of a subject according to an exemplary embodiment consistent with the present invention.

In accordance with embodiments consistent with the present disclosure, FIG. 1 shows a brain-state assessment device 10 for acquiring and processing brain electrical signals using Bx™ technology, and providing an evaluation of the subject's brain functionality. In an exemplary embodiment, the brain-state assessment device is implemented as a portable device to facilitate point-of-care applications. This device consists of a patient sensor 40 which may be coupled to a base unit 42, which can be handheld, as illustrated in FIG. 1. Patient sensor 40 includes an electrode array 35 comprising at least one disposable neurological electrode to be attached to a patient's head to acquire brain electrical signals. The electrodes are configured for sensing both spontaneous brain activity as well as evoked potentials generated in response to applied stimuli, e.g., audio, visual or tactile stimuli. A simplest embodiment of the apparatus comprises of five (active) channels and three reference channels. The electrode array 35 consists of anterior (frontal) electrodes: F1, F2, F7, F8, Fz', and Fpz (reference electrode) to be attached to a subject's forehead, and electrodes A1 and A2 to be placed on the front or back side of the ear lobes, in accordance with the International 10/20 electrode placement system (with the exception of Fz'). The use of a limited number of electrodes enables rapid and repeatable placement of the electrodes on a subject, which in turn facilitates efficient, and more accurate, patient monitoring. Further, in one embodiment, the electrodes may be positioned on a low-cost, disposable platform, which can serve as a "one-size-fits-all" sensor. For example, electrodes 35 may be positioned on a head gear that is configured for easy and/or rapid placement on a patient. Other electrode configurations may be utilized as and when required, as would be understood by those of ordinary skill in the art.

The base unit 42 primarily includes an analog electronics module 30, a digital electronics module 50, user interface 46, stimulus generator 54 and battery 44 as illustrated in FIG. 1. The analog electronics module receives signals from one or more of the neurological electrodes operatively connected through the electrical cable 41a. The analog module is configured to amplify, filter, and preprocess the analog waveforms acquired from the electrode channels. The analog module 30 may further include an analog-to-digital converter (ADC) to digitize the received analog signal. Digital electronics module 50 can then process the digitized data acquired through analog module 30 and can perform data analysis to aid in interpretation of data pertaining to brain electrical activity. Further, as shown in FIG. 1, the digital electronics module 50 may be operatively connected with a number of additional device components.

The digital electronics module 50 comprises a digital signal processor (DSP) 51 for processing the data corresponding to the acquired brain electrical signals, and a memory 52 which stores the instructions for processing the data, such as a DSP algorithm. The processor 51 is configured to perform the following tasks:

a) Automatic identification and removal of several types of non brain-generated artifacts from the acquired brain electrical signal data;

b) Extraction of quantitative signal features;

c) Classification based on Linear Discriminant Analysis (LDA), using pre-selected subsets of age-normalized features (z-scores); and d) Derivation of abnormality indices indicative of a subject's brain function.

The processor 51 is configured to implement the DSP algorithm to identify data that is contaminated by non brain-generated artifacts, such as eye movements, electromyographic activity (EMG) produced by muscle tension, spike (impulse), external noise, etc. In one embodiment, artifact identification is performed using as input the signals from the five active leads Fp1, Fp2, F7, F8, Fz' referenced to linked ears (A1+A2)/2, and sampled at 100 Hz. Incoming data epochs of 2.56 seconds (256 samples per epoch) are split into 8 basic data units (sub-epochs) of length 320 ms (32 data points per sub-epoch). Artifact identification is done on a per-sub-epoch basis and guard bands are implemented around identified artifact segments of each type. Artifact-free epochs are then constructed from at most two continuous data segments, with each data segment being no shorter than 960 ms (which corresponds to the time span of 3 contiguous sub-epochs). The resulting artifact-free data is then processed to extract signal features and classify the extracted features to provide an assessment of brain function. In another embodiment, denoising is performed using a signal processing method described in commonly-assigned U.S. patent application Ser. No. 12/106,699, which is incorporated herein by reference in its entirety. In one embodiment consistent with the present disclosure, the artifact identification and rejection algorithm follows the following steps:

a. Transforming the signal into a plurality of signal components;

b. Computing fractal dimension of the components;

c. Identifying noise components based on their fractal dimension;

d. Automatically attenuating the identified noise components;

e. Reconstructing a denoised signal using inverse transform.

The input analog brain electrical signal is at first digitized and then deconstructed into its constitutive coefficients using a linear or non-linear signal transformation method, such as Fast Fourier Transform, Independent Component Analysis (ICA)-based transform, wavelet transform, wavelet packet transform etc. The fractal dimensions of the coefficients are then calculated in the transform domain, and the coefficients that have a fractal dimension higher than a preset threshold value are attenuated. The intact and re-scaled coefficients are then remixed using an inverse signal transform to generate a denoised signal, which is further processed to extract signal features and classify the extracted features.

Processor 51 is configured to execute instructions contained in memory 52 to perform an algorithm for quantitative feature extraction from denoised signals. The feature extraction algorithm takes as input a number of "artifact-free" or "denoised" epochs having a temporal length of 2.56 seconds, which corresponds to 256 samples for data sampled at 100 Hz. In an exemplary embodiment, processor 51 is configured to perform a linear feature extraction algorithm based on Fast Fourier Transform (FFT) and power spectral analysis, according to a method disclosed in commonly-assigned U.S. patent application Ser. Nos. 11/195,001 and 12/041,106, which are incorporated herein by reference in their entirety. In short, the algorithm performs feature selection using Fourier transform of narrow frequency bands and calculating the power at each frequency band. The frequency composition can be analyzed by dividing the signal into the traditional frequency bands: delta (1.5-3.5 Hz), theta (3.5-7.5 Hz), alpha (7.5-12.5 Hz), beta (12.5-25 Hz), and gamma (25-50 Hz). Higher frequencies, up to and beyond 1000 Hz may also be used. Univariate features are computed by calculating the absolute and relative power for each of the electrodes or between a pair of electrodes within selected frequency bands, and the asymmetry and coherence relationships among these spectral measurements within and between the sets of electrodes. The processor 51 may also be configured to compute multivariate features, which are non-linear functions of groups of the univariate features involving two or more electrodes or multiple frequency bands. The computed measures are normalized by performing age-regression and Z-transformation to obtain features (Z-scores) for discriminant analysis.

In another embodiment, processor 51 is configured to perform a linear feature extraction algorithm based on wavelet transforms, such as Discrete Wavelet Transform (DWT) or Complex Wavelet Transforms (CWT). In yet another embodiment, processor 51 is configured to perform feature extraction using non-linear signal transform methods, such as wavelet packet transform. The features extracted by this method are referred to as Local Discriminant Basis (LDB) features. The LDB algorithm defines a set of features that are optimized for the statistical discrimination between different classes of signals. The computation of these features begins with the calculation of power spectral densities over a set of epochs for each electrode channel. For each subject, the algorithm produces one power spectrum for each channel, and quotients of the power spectra for each pair of channels are then calculated. Thus, for a 5 channel system, a set of 15 power spectra per subject is produced, which allows for the calculation of 15 distinct bases (sets of LDB vectors). The LDB features are then obtained by calculating a wavelet packet table for each power spectrum using the Haar wavelet function. The function is applied to both the low pass and the high pass sub-bands, which generates a tree structure providing many possible wavelet packet bases, and accordingly, signals are decomposed into a time-frequency dictionary.

In another embodiment consistent with the present disclosure, diffusion geometric analysis is used to extract non-linear features according to a method disclosed in commonly-assigned U.S. patent application Ser. No. 12/105,439, which is incorporated herein by reference in its entirety.

The extracted signal features (such as the diffusion geometry features, Local Discriminant Basis features, FFT features, etc.) are classified into brain-state categories using a classification algorithm, such as Linear Discriminant Analysis (LDA). All the extracted features are age-regressed and z-transformed for discriminant analysis. The LDA optimally combines the features (Z-scores) into a discriminant output/score that possesses the maximum discriminating power. In one embodiment, the discriminant analysis used is a two category linear classifier (also called "dichotomizer" or "binary test") which assigns for each given subject a discriminant score (a real-valued number) between 0 and 100. The classification rule which is commonly associated with linear discriminant functions is the following: after a cut-off threshold T is selected (for example, but not necessarily, in the middle of the discriminate score range i.e. T=50), the classifier assigns any subject with a discriminant score $g \leq T$ to the category "brain state A" and assigns any subject with a score $g > T$ to the category "brain state B.". A score "lower than 50" indicates that the subject is more likely to belong to brain state A than to brain state B, and vice versa. Examples of different classification classes include, but is not limited to, normal vs. abnormal, organic vs. functional, focal vs. diffused, etc. The discriminant scores, $g_A$ and $g_B$ corresponding to classes A and B, are computed for any subject with the following Fisher LDA formulas:

$$g_A = 100 \cdot G(1)/(G(1)+G(2)), g_B = 100 \cdot G(2)/(G(1)+G(2))$$

$$G(1) = \exp(Z \cdot W_A + C_A), G(2) = \exp(Z \cdot W_B + C_B)$$

where Z denote the vector of age-regressed z-transformed features computed for any subject. Note that since $g_B = 100 - g_A$, only $g_A$ is addressed in the remainder of this document, and is referred to as the "discriminant output/score" and simply denoted by g (or g(Z) to emphasize that it is a function of the z-transformed features). $W_A$ and $W_B$ denote two weight vectors that are derived from a reference database, and $C_A$ and $C_B$ are two constants which are commonly called bias or threshold weights. The weights and constants entirely define the linear discriminant function and are pre-selected using a training routine such that they result in the 'best' separation between the classes. The weights for the different monopolar and/or bipolar univariate and multivariate features may be estimated from a stored population reference database, such as a database comprising of population normative data indicative of brain electrical activity of a first plurality of individuals having normal brain state, or population reference data indicative of brain electrical activity of a second plurality of individuals having an abnormal brain state. Similarly, the weights may be selected from a database of the subjects own brain electrical activity data generated in the absence or presence of an abnormal brain state. In some embodiments, the classification task may be performed using one or more linear discriminant functions, and in such a case, the discriminant outputs may be combined using a majority voting rule.

In some embodiments, the discriminant scores can be further converted to probabilities of correct and incorrect classification using Receiver Operating Characteristics (ROC) curves, if the true classification information (diagnosis) for a sample group is available. For a given linear discriminant-based classifier, e.g. of normal/abnormal brain function, the ROC curve indicates the sensitivity, specificity, positive predictive value (PPV), and negative predictive value (NPV) which can be expected from this particular algorithm/classifier at different values of the classification threshold T. For a "Normal" vs. "Abnormal" discriminant, "Normal" may be referred to as "disease absent" and "Abnormal" as "disease present". Using this convention, sensitivity of the classifier is defined as the ratio of "true positives" over the number of subjects in the sample group for whom "disease" is present. Specificity of the classifier is defined as the ratio of "true negatives" over the number of subjects in the sample group for whom "disease" is absent. PPV is defined as the probability that "disease" is present when the test result is positive, and NPV is defined as the probability that "disease" is absent when the test result is negative.

Figure 2A:
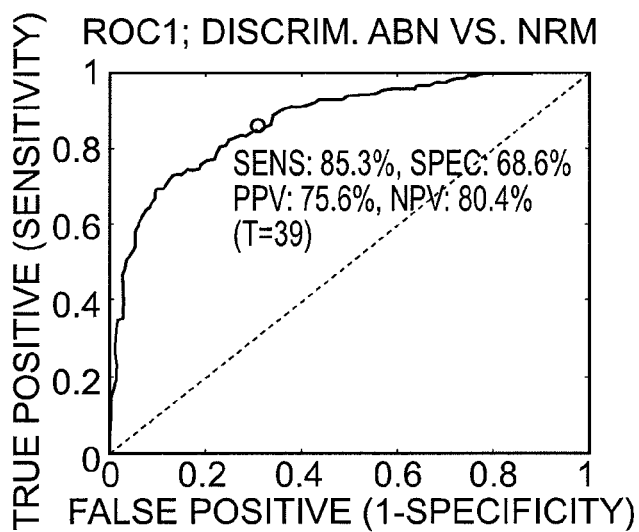
FIGS. 2A and 2B illustrate the performance of a normal/abnormal classifier for a sample group of 396 subjects.
Figure 2B:
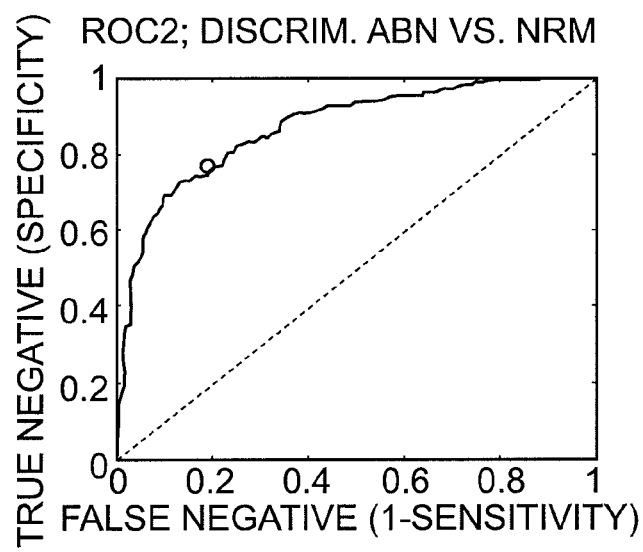
Figure 2C:
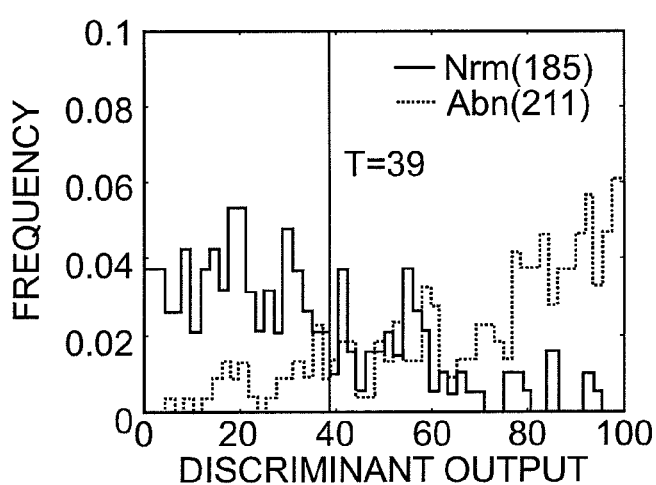
FIG. 2C illustrates the distribution of discriminant outputs (scores) for a normal/abnormal classifier for a sample group of 396 subjects.

As described earlier, the output of a two-state discriminant analysis is a number g(Z) that can take any value between 0 and 100. Once a critical value (or threshold) T is selected, the output of the test becomes binary, and sensitivity and specificity for that particular threshold can be calculated. The ROC is the curve through the set of points: $\{(1\text{-specificity}(T), \text{sensitivity}(T))\}$, which is obtained by varying the value of the threshold T in fixed increments between 0 and 100. FIG. 2A-C illustrates ROC curves and histogram of discriminant scores for a normal/abnormal classifier comprising a sample group of 396 subjects. The abnormal group of 211 subjects comprised individuals suffering from dementia, encephalopaties, migraine, head injury, and several other abnormal brain conditions. As shown in the FIGS. 2A and 2B, the ROC curves illustrate the achievable statistical performance of the normal/abnormal classifier for a threshold value T=39. The threshold T=39 was selected to achieve the highest sensitivity and specificity for the classification. One of ordinary skill in the art will understand that any other type of classifier (for example, Partial Least Squares classifier, quadratic classifier, etc.) may also be used in place of LDA, and that the data is not sensitive to the choice of classifier.

In yet another embodiment, instead of producing a binary classification result, such as a determination of "Normal" or "Abnormal" based on the discriminant score, processor 51 is configured to compute an index, which reflects the probability of correctness of the brain state classifier. For example, in a normal vs. abnormal classification, the discriminant output may be represented using a probabilistic "Brain Abnormality Index" (BAI) instead of a binary classification result. Similarly, for a focal vs. diffused classification, the discriminant output may be represented using "Brain Focality Index" (BFI), which would reflect the probability of the classification being accurate.

Figure 3A:
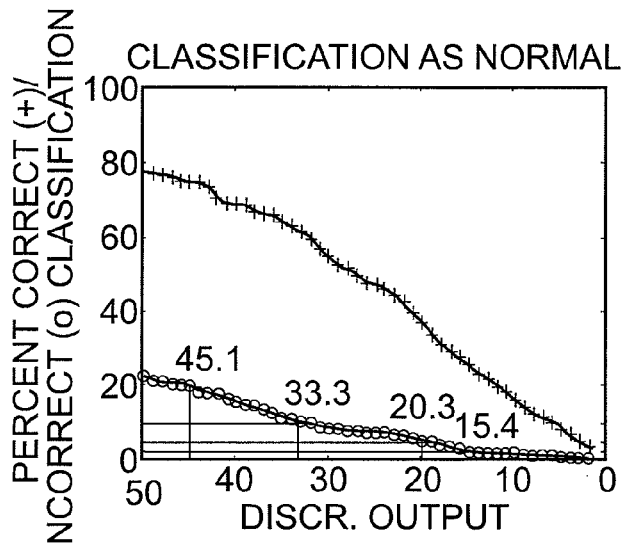
FIGS. 3A and 3B show Classification Accuracy curves for a normal/abnormal classifier for a sample group of 396 subjects.
Figure 3B:
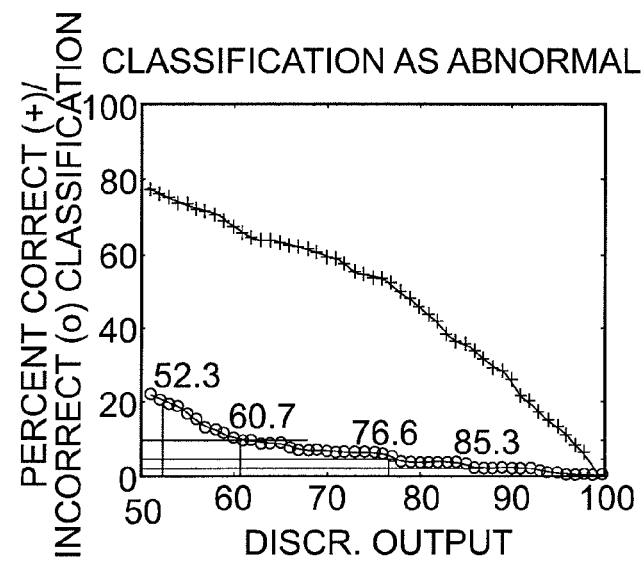

The probability index is calculated using Classification Accuracy Curves (CAC) which are derived from the ROC curves described earlier. The method of calculating a probability index will be explained herein using normal vs. abnormal classification as an example. As can be seen in FIG. 2C, the distributions of discriminant scores for subjects with "normal brain function" ("normals") and subjects with "abnormal brain function" ("abnormals") overlap. Therefore, choosing a discriminant score threshold T between 0 and 100 may result in some normal subjects being misclassified as "abnormal" (and vice-versa). If the threshold T is reduced, the percentage of normal subjects being correctly classified as "normal" (specificity) decreases, and the percentage of abnormal subjects classified as "abnormal" (sensitivity) increases. FIG. 3A shows the percentage of correct classification of normal subjects as "normal" and the percentage of incorrect classification of abnormal subjects as "normal" as the discriminant score threshold goes from 50 to 0. Similarly, FIG. 3B shows the percentage of correct classification of abnormal subjects as "abnormal" and the percentage of incorrect classification of normal subjects as "abnormal" as the discriminant score threshold goes from 50 to 100. These two graphs are referred to as the Classification Accuracy Curves (CACs) for the discriminant function using the given test sample. Specifying tolerance for misclassification in the form of maximum misclassification percentages (e.g. 2%, 5%, 10% and 20%), the corresponding discriminant score thresholds can be derived from the CAC curves. In FIG. 3A, the thresholds: 15.4, 20.3, 33.3 and 45.1 correspond to misclassification percentages of 2%, 5%, 10% and 20%. That is, if the discriminant output threshold is selected as 15.4, only 2% of the abnormal subjects in the given test sample will be incorrectly classified as normal. Similarly, in FIG. 3B, the thresholds: 85.3, 76.6, 60.7 and 52.3 correspond to misclassification percentages of the normal subjects in the given test sample of 2%, 5%, 10% and 20% respectively.

The CAC curves are then used to calculate the BAI index which is used to report, in probabilistic fashion, the result of a subject's brain function classification. The BAI index is an objective probabilistic classification index which is derived in the following way. From the CAC curve showing misclassification of abnormal subjects as "normal" (also called false negatives), as shown in FIG. 3A, fifty values of the classification threshold (denoted $T_1, \ldots T_{50}$) are determined, such that: with the discriminant threshold set at $T_1$ the misclassification rate of abnormals is 1% i.e. the probability of a subject with a discriminant score g in the range $g \leq T_1$ of being normal is 99%, with the discriminant threshold set at $T_2$ the misclassification rate of abnormals is 2% i.e. the probability of a subject with a discriminant score g in the range $g \leq T_2$ of being normal is 98%, and so on. Finally, $T_{50}$ is determined so that with the discriminant threshold set at $T_{50}$ the misclassification rate of abnormals is 50% i.e. the probability of a subject with a discriminant score g in the range $g \leq T_{50}$ of being normal is 50%. Similarly, from the CAC curve showing misclassification of normal subjects as "abnormal" (also called false positives), as shown in FIG. 3B, fifty values of the threshold (denoted $T_{100}, \ldots T_{51}$) are determined, such that: with the discriminant threshold set at $T_{100}$ the misclassification rate of normals is 1% i.e. the probability of a subject with a discriminant score g in the range $g > T_{100}$ of being abnormal is 99%, with the discriminant threshold set at $T_{99}$ the misclassification rate of normals is 2% i.e. the probability of a subject with a discriminant score g in the range $g > T_{99}$ of being abnormal is 98%, and so on. Finally, $T_{51}$ is determined so that with the discriminant threshold set at $T_{51}$ the misclassification rate of normals is 50% i.e. the probability of a subject with a discriminant score g in the range $g > T_{51}$ of being abnormal is 50%. In addition, $T_0$ and $T_{101}$ are defined as the extreme values of discriminant outputs, namely: $T_0=0$ and $T_{101}=100$.

Figure 3C:
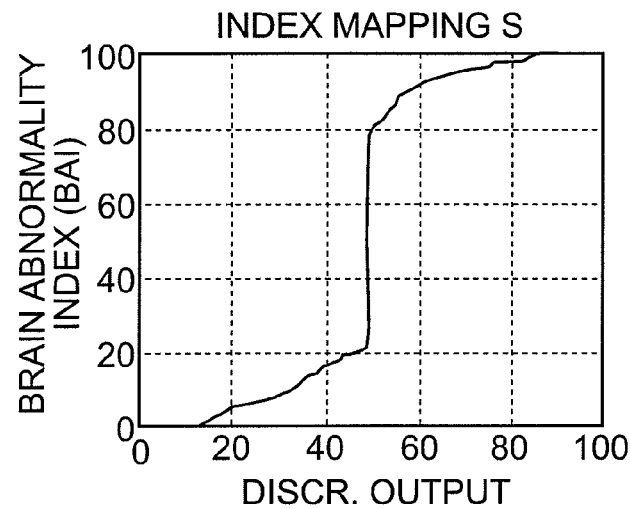
FIG. 3C illustrates a non-linear S-shaped mapping S for a normal/abnormal classifier which is data-driven and is used to convert the scalar output of a linear discriminant function into an objective probabilistic index (BAI).

These values of $T_k$ are used to map a discriminant score (which carries no probabilistic significance) to an objective probabilistic index which is referred to as Brain Abnormality Index (BAI). This index can take any one of the 100 integer values in the range $\{1, \ldots 100\}$. The mapping is done in the following way. If the discriminant score g of the classification falls in the bin $[T_{k-1}, T_k)$, where $k=\{1, \ldots, 50\}$, then BAI is equal to k. Note that [a, b) denotes the range of values of variable x such that $a \leq x < b$. On the other hand, if the discriminant score g falls in the bin $[T_{k-1}, T_k)$, where $k=\{51, \ldots 101\}$, then BAI is equal to k−1. By plotting the BAI values against the values of $T_k$, a non-linear S-shaped mapping S is obtained, as shown in FIG. 3C. As was explained in the above paragraph, a subject with a BAI index of x ($x \leq 50$) reflects that the probability of this subject having normal brain function is 100−x (based on the statistical sample of subjects used to derive the CAC curves). Similarly, a subject with a BAI index of x ($x \geq 50$) reflects that the probability of this subject having abnormal brain function is x−1 (based on the statistical sample of subjects used to derive the CAC curves). Note that the above construction was meant to produce 100 possible values of the BAI index but that a construction yielding any number P (with the requirement that $P \geq 2$) of possible index values could be similarly derived. Note that the construction of the non-linear mapping S is entirely determined by the classification performance data and is therefore entirely "data-driven."

Figure 4A:
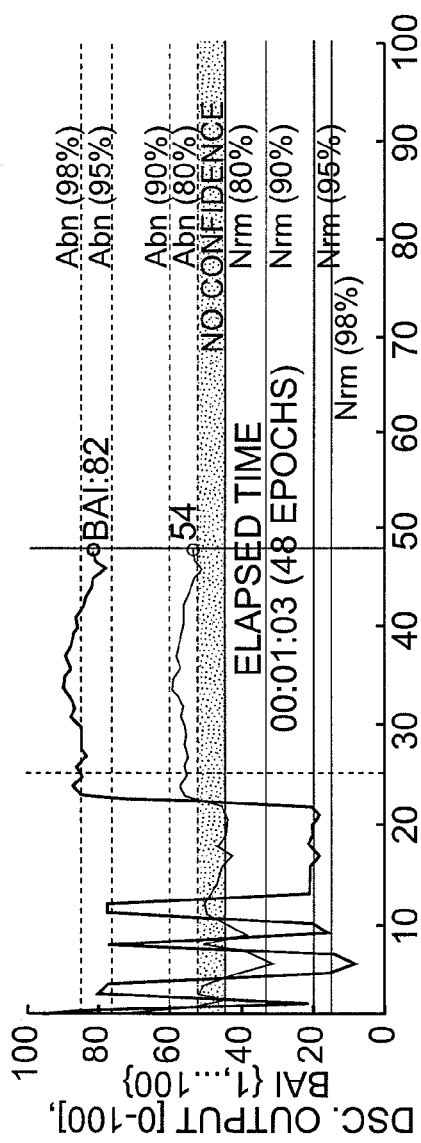
FIG. 4A shows the evolution of discriminant outputs as a function of number of acquired clean signal epochs, and the corresponding evolution of the BAI index, for a normal/abnormal classification in case of a subject diagnosed with a "stroke".
Figure 4B:
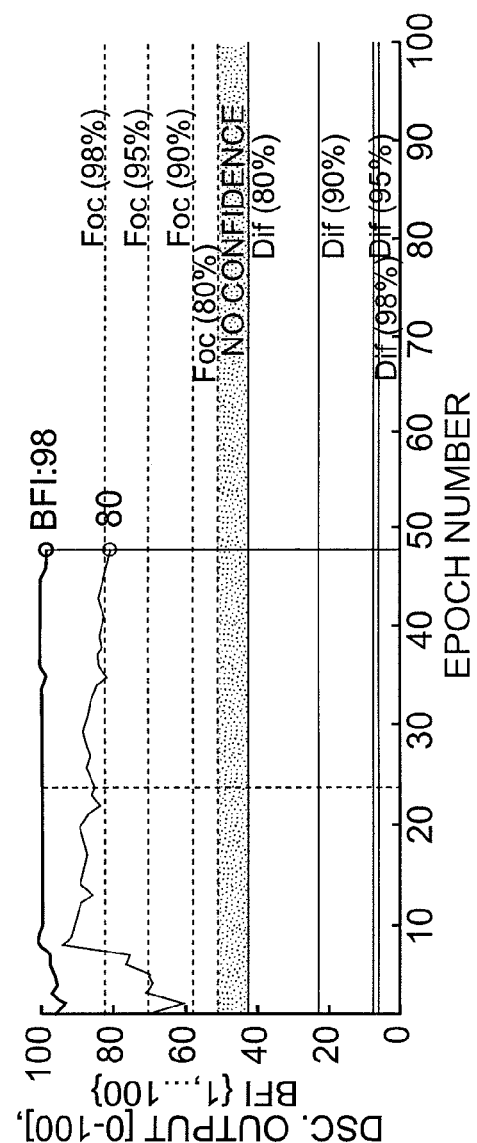
FIG. 4B shows the evolution of discriminant outputs and the corresponding evolution of the BFI index, for a focal/diffuse classification in case of a subject diagnosed with a "stroke".
Figure 5:
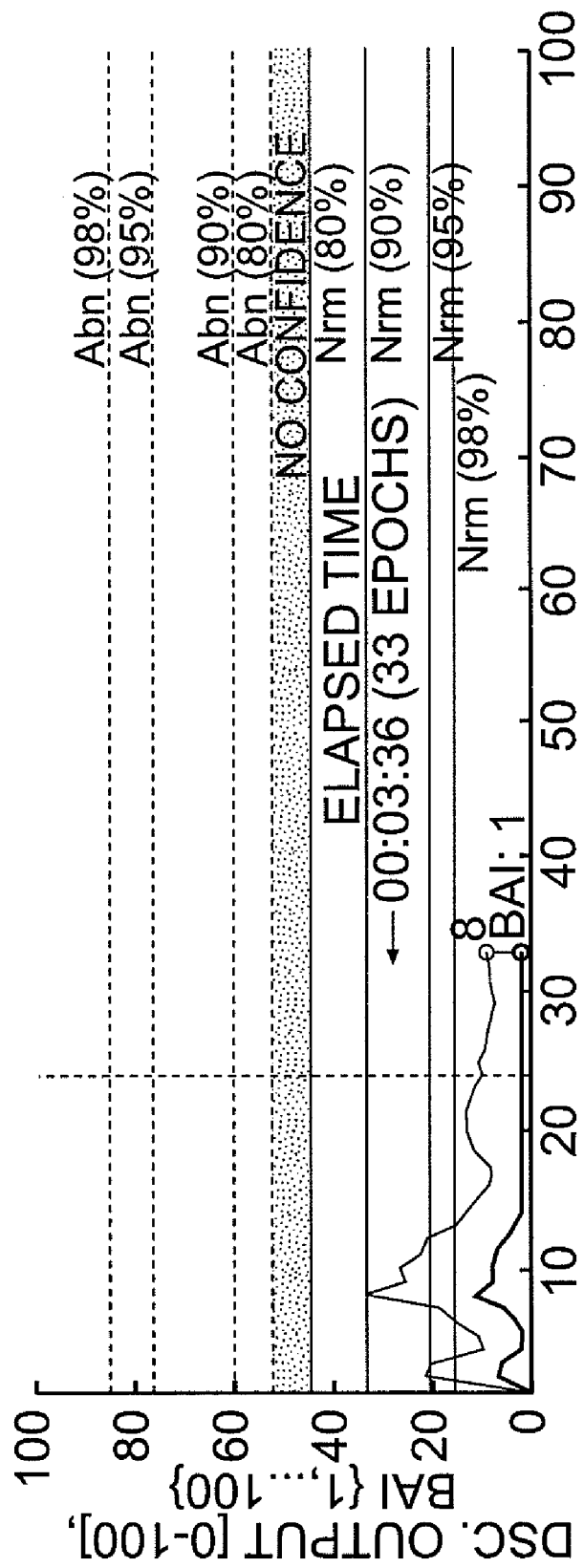
FIG. 5 shows the evolution of discriminant outputs and the corresponding evolution of the BAI index, for a normal/abnormal classification in case of a "normal" subject.

Using the method described above, the probability of correctness of the classification result produced by any two-state classifier can be derived. The probability index can also be represented as a function of the incoming data epochs to show the evolution or change in brain electrical signal over time. FIGS. 4A and 4B show the behavior of the Brain Abnormality Index (BAI) and Brain Focality Index (BFI) as a function of clean epochs collected for a subject diagnosed with a stroke. As shown in the figure, the "Normal" vs. "Abnormal" classification result is within the "Abnormal, 95% confidence" zone (Brain Abnormality Index: 82), and therefore, the subject was correctly classified as "Abnormal." A second classification step was then performed to identify whether the abnormality in brain function was diffuse or focal. As shown in the figure, the "Diffuse" vs. "Focal" discriminant score fell in the "Diffuse, 98% confidence" zone (Brain Focality Index: 98, Brain Diffuseness Index: 2). Therefore, the subject's brain state was correctly classified as "Focal". FIG. 5 shows the evolution of BAI as a function of incoming data epochs for a normal subject. The "Normal vs. "Abnormal" test results were within the "Normal, 98% confidence" zone (Brain Abnormality Index: 1). Thus, the subject was correctly classified as "Normal", and further classification (such as "Diffuse vs. "Focal") was not performed.

Figure 6:
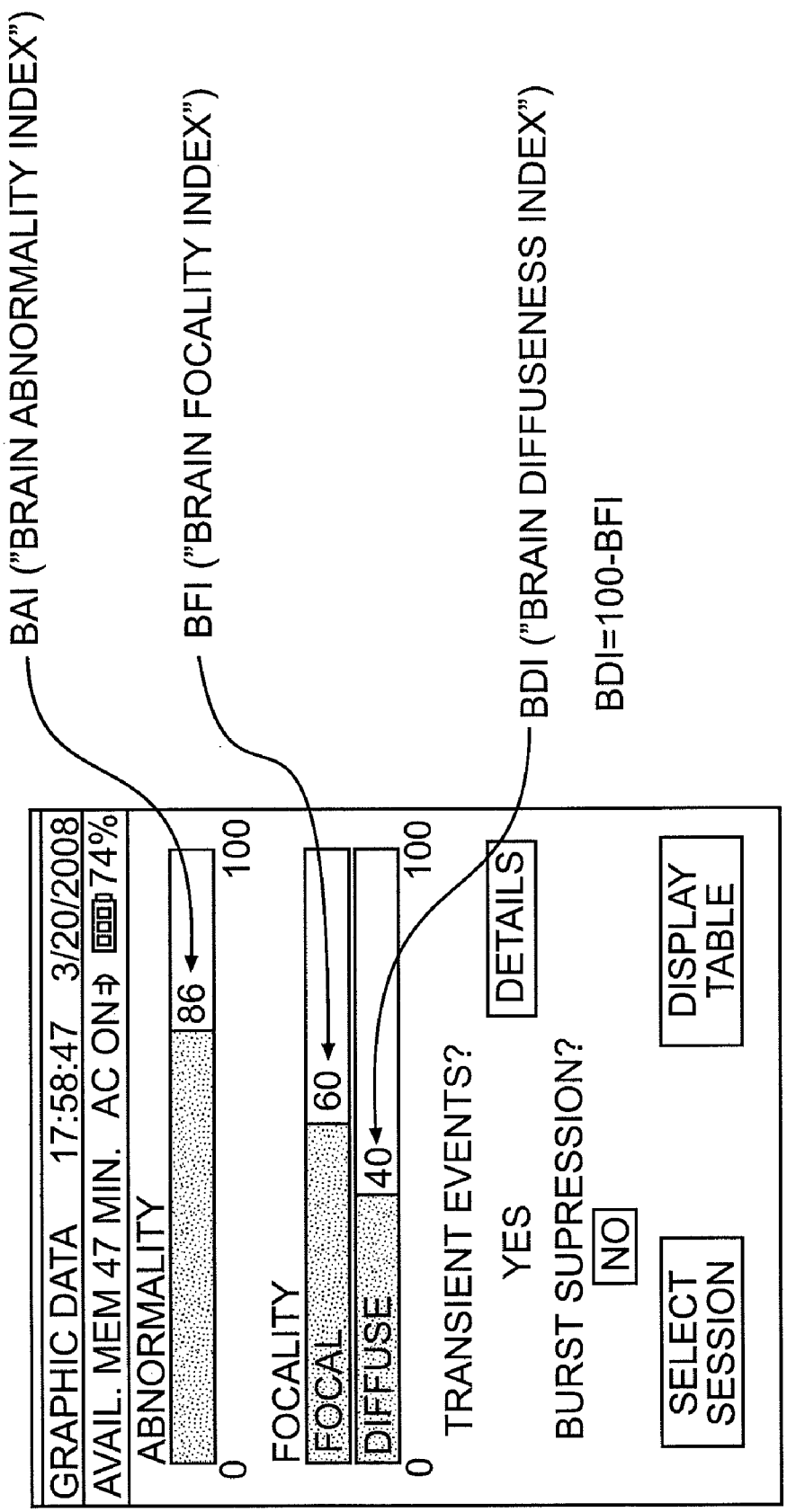
FIG. 6 illustrates a graphic data screen for a device for recording and processing brain electrical signals according to an exemplary embodiment consistent with the present invention.

In an embodiment consistent with the present disclosure and the Bx™ technology, the user interface 46 of device 10 is configured to display the classification probability indices graphically. As shown in FIG. 6, the device provides a graphic data screen showing a horizontal index bar with numerical indications of "Abnormality" and "Focality". The user interface 46 may further display a Detailed Data screen, which would provide access to detailed data about the features that made the largest contribution to the abnormal classification. From this screen, the user would be able to access tabular screens showing values of the quantitative features and the Z-scores for each feature extracted from the artifact-free data epochs.

Figure 7:
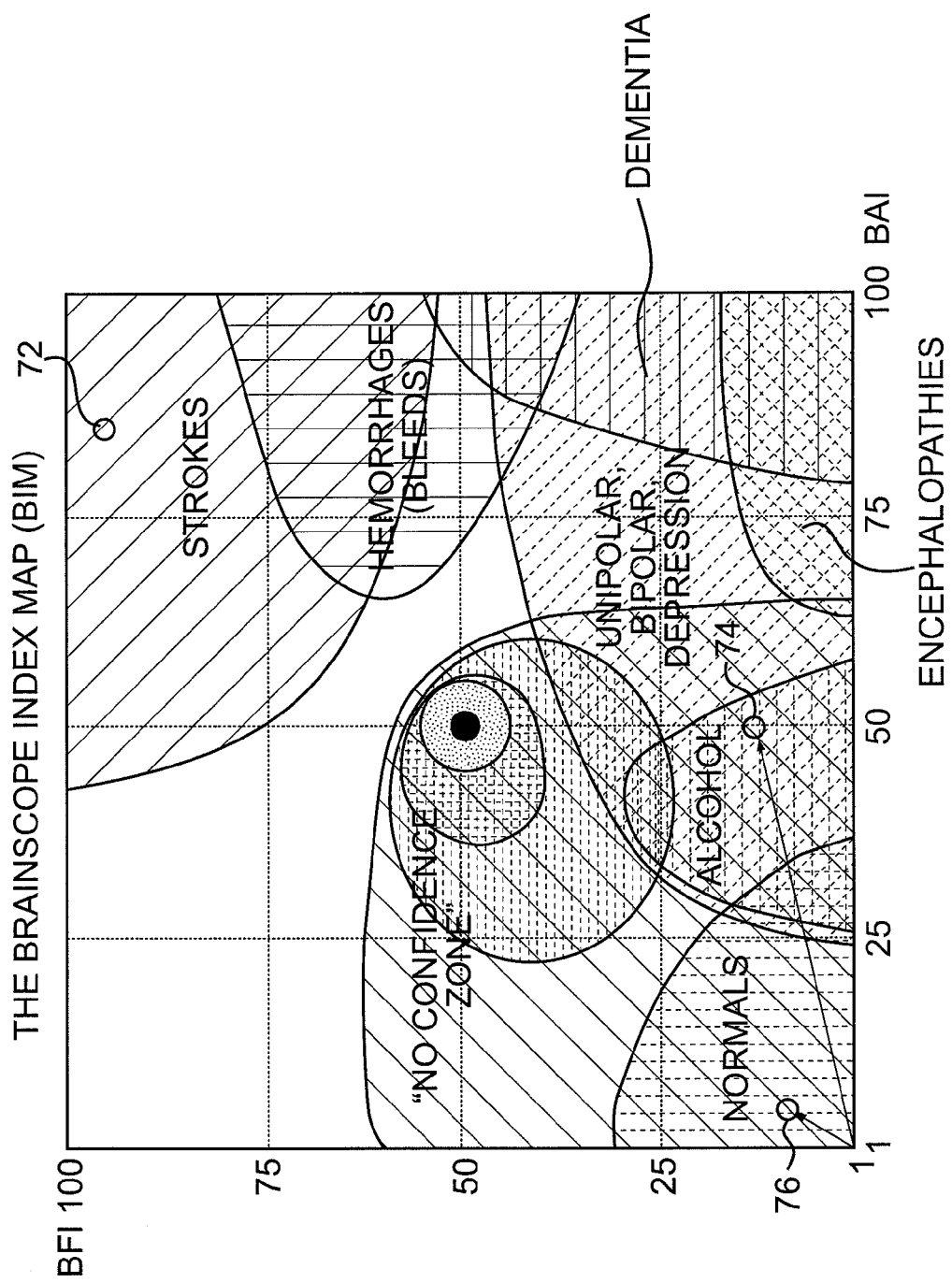
FIG. 7 illustrates Brain Abnormality Vectors presented on a BrainScope Index Map (BIM) for three different subjects.
Figure 8:
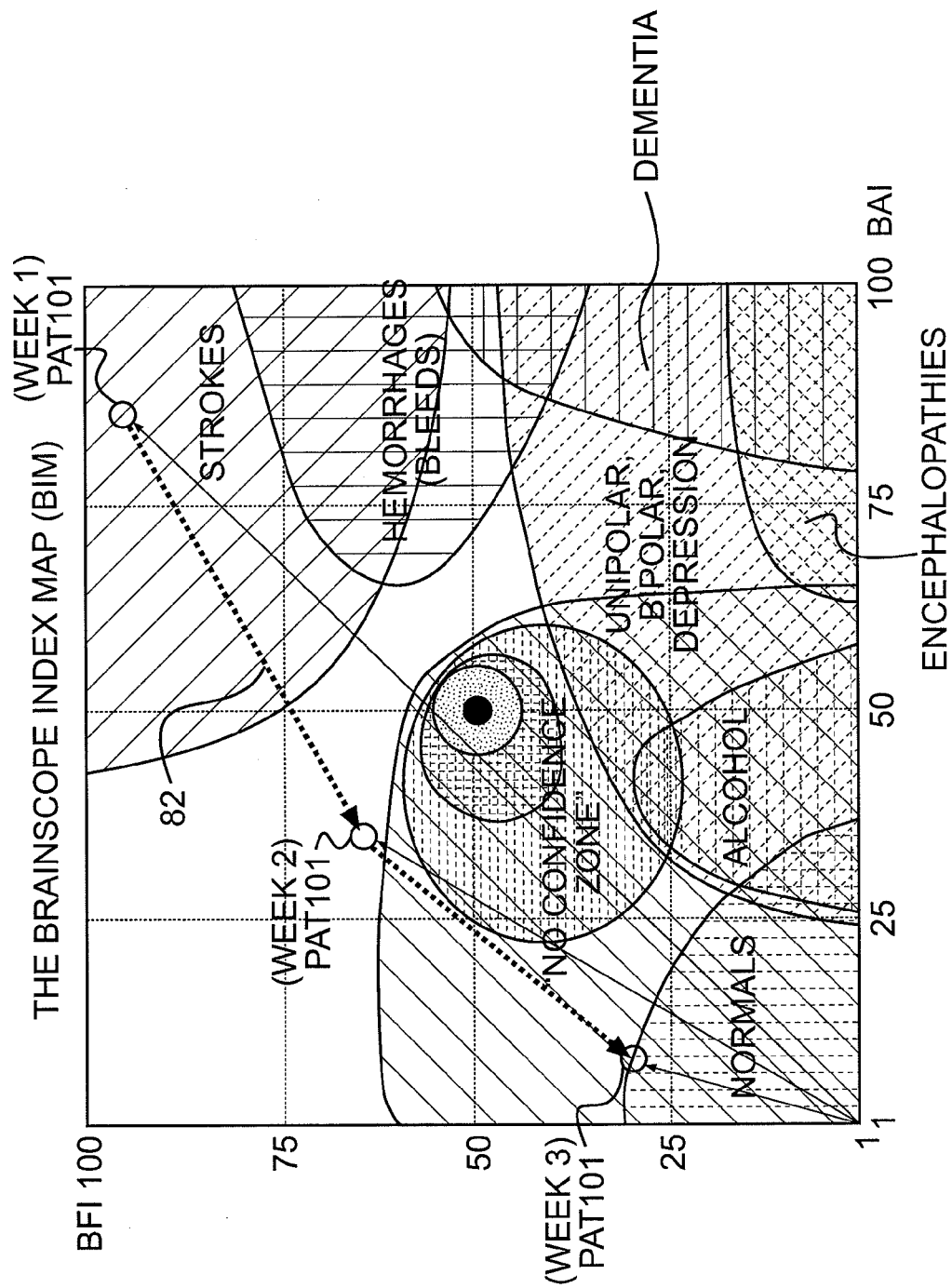
FIG. 8 illustrates a Brain Abnormality Vector on a BrainScope Index Map (BIM) for tracking the recovery or disease progression in a subject.

In another embodiment, the results of the neurometric analysis, such as the BAI and BFI indices, are reported in the form of a 2-dimensional "BrainScope Abnormality Vector" (BAV) on the user interface 46. In yet another embodiment, the BAV is superimposed on a BrainScope Index Map (BIM), which reflects the BAI and BFI values associated with different neurological states or brain dysfunctions. More specifically, a BrainScope Index Map is a graphical plot of the BAI and BFI generated from the reference database used to develop the indices. The BAI and BFI values associated with a particular brain state cluster together on the map, thereby, creating different regions or sections on the map that can be attributed to specific brain states, as shown in FIGS. 7 and 8. Non-linear decision boundaries corresponding to the clusters on the map may be drawn to partition the map into specific brain state regions. The BIM may be generated offline using the reference database, and may be stored in the memory 52 of the base unit 42. FIG. 7 shows BAVs 72, 74 and 76 for three different subjects plotted on a BrainScope Index Map (BIM). Based on these abnormality vectors, patient 72 may be diagnosed with a "stroke", patient 74's condition may be associated with "alcohol" and patient 76 may be identified as "normal". In yet another embodiment, the abnormality vectors of multiple tests performed sequentially on a subject over a period of time are plotted on a BIM as a trajectory 82 to chart the course of recovery or progression of a neurological condition, as shown in FIG. 8.

Further, in an embodiment consistent with the Bx™ technology, the BIM stored in the memory 52 may be revised or re-plotted by the users of the brain-state assessment device 10 based on the diagnostic outcomes of their own subject population. This would allow users to incorporate new data into the BIM, and add new segments or regions associated with brain dysfunctions not included in the initial map. Similarly, the decision boundaries on the BIM may reconfigured by the users based on how the different brain states cluster on the BIM.

In another embodiment consistent with Bx™ technology, if a subject is identified as "abnormal", the processor 51 initializes further discriminant classification tasks (such as, "normal" vs. "stroke", "normal" vs. "dementia", etc.) to elucidate what condition resulted in the "abnormal" classification. The additional discriminant classifications provide abnormality indices for specific brain abnormalities. For example, linear discriminant classification between a group of "normal" subjects and subjects diagnosed with a "stroke" or "bleed" provides a Brain Abnormality Index for abnormal brain function of type "Stroke or Bleed" (BAI_SB). Similarly, linear discriminant classification between a group of "normal" subjects and "heavily drunk" subjects provide a Brain Abnormality Index for abnormal brain function of type "Alcohol" (BAI_Alc). In some embodiments, a brain abnormality profile is used to report the abnormality indices associated with different brain states, which could potentially solve the problem of multiple disorders (such as stroke and alcohol, stroke and dementia, etc.) where the user could be uncertain which abnormality dominates in the normal vs. abnormal classification. The abnormality profile shown in FIG. 9, for example, helps to correctly classify a heavily drunk person as a stroke patient, since both the "BAI_SB" and "BAI_Alc" values are raised. That is, the BAI and the BFI values are correctly attributed to the stroke condition.

Referring again to FIG. 1, the memory 52 of brain-state assessment device 10 may further contain interactive instructions for using and operating the device to be displayed on the screen of the user interface 46. The instructions may comprise an interactive feature-rich presentation including a multimedia recording providing audio/video instructions for operating the device, or alternatively simple text, displayed on the screen, illustrating step-by-step instructions for operating and using the device. The inclusion of interactive instructions with the device eliminates the need for extensive training for use, allowing for deployment and use by persons other than medical professionals. The memory 52 may also contain the reference database. In an exemplary embodiment, the database may be accessed from a remote storage device via a wireless or a wired connection. Similarly, data collected from the subject by the brain-state assessment device 10 may be recorded in the database for future reference.

The brain-state assessment device 10 can be a standalone system or can operate in conjunction with a mobile or stationary device to facilitate display or storage of data, and to signal healthcare personnel when therapeutic action is needed, thereby facilitating early recognition of emergency conditions. Mobile devices can include, but are not limited to, handheld devices and wireless devices distant from, and in communication with, the device. Stationary devices can include, but are not limited to, desktop computers, printers and other peripherals that display or store the results of the neurological evaluation. In an exemplary embodiment, the brain-state assessment device 10 stores each patient file, which includes a summary of the session and test results, on a removable memory card 47, such as compact flash (CF) card. The user can then use the memory card 47 to transfer patient information and procedural data to a computer, or to produce a printout of the data and session summary. In another embodiment, results from the processor 51 are transferred directly to an external mobile or stationary device to facilitate display or storage of data. For example, the results from the processor 51 may be displayed or stored on a PC 48 connected to the base unit 42 using a PC interface, such as an USB port, IRDA port, BLUETOOTH® or other wireless link. In yet another embodiment, the results can be transmitted wirelessly or via a cable to a printer 49 that prints the results to be used by attending medical personnel. Further, the brain-state assessment device 10 can transmit data to another mobile or stationary device to facilitate more complex data processing or analysis. For example, the device, operating in conjunction with PC 48, can send data to be further processed by the computer. In another embodiment consistent with the Bx™ technology, the processor 50 transmits a raw, unprocessed signal acquired from a subject to PC 48 for analyzing the recorded data and outputting the results. The unprocessed brain electrical signals recorded from a subject may also be stored in a remote database for future reference and/or additional signal processing.

In an embodiment consistent with the present disclosure and the Bx™ technology, user interface 46 may be configured to communicate patient information and/or procedural data to attending medical personnel, such as an ER physician, a triage nurse, or an emergency response technician. Information that is conveyed through user interface 46 can include a variety of different data types, including, but not limited to, diagnostic results (such as the Brain Abnormality Vector displayed on BIM), intermediate analysis results, usage settings, etc. In another exemplary embodiment, user interface 46 may receive and display usage setting information, such as the name, age and/or other statistics pertaining to the patient. The user interface 46 comprises a touchscreen interface for entering the user input. A virtual keypad may be provided on the touchscreen interface for input of patient record fields.

In an embodiment consistent with the present invention and the Bx™ technology, the base unit 42 includes a stimulus generator 54, which is operatively coupled to the processor 51, for applying stimuli to the subject to elicit evoked potential signals. Additionally, base unit 42 contains an internal rechargeable battery 44 that can be charged during or in between uses by battery charger 39 connected to an AC outlet 37.

The brain-state assessment device 10, developed in accordance with the Bx™ technology, is designed for near-patient testing in emergency rooms, ambulatory setting, and other field applications. The device is intended to be used in conjunction with CT scan, MRI or other imaging studies to provide complementary or corroborative information about a patient's brain functionality. The key objective of point-of-care brain state assessment is to provide fast results indicating the severity of a patient's neurological condition, so that appropriate treatment can be quickly provided, leading to an improved overall clinical outcome. For example, the device may be used by an EMT, ER nurse, or any other medical professional during an initial patient processing in the ER or ambulatory setting, which will assist in identifying the patients with emergency neurological conditions. It will also help ER physicians in corroborating an immediate course of action, prioritizing patients for imaging, or determining if immediate referral to a neurologist or neurosurgeon is required. This in turn will also enable ER personnel to optimize the utilization of resources (e.g., physicians' time, use of imaging tests, neuro consults, etc.) in order to provide safe and immediate care to all patients.

In addition, the brain-state assessment device 10 is designed to be field-portable, that is, it can be used in locations far removed from a full-service clinic—for example, in remote battlefield situations distant from military healthcare systems, during sporting events for identifying if an injured athlete should be transported for emergency treatment, at a scene of mass casualty in order to identify patients who need critical attention and immediate transport to the hospital, or at any other remote location where there is limited access to well-trained medical technicians.

Embodiments consistent with the present invention, using advanced signal processing algorithms and stored data of the brain activity of thousands of subjects having different neurological indications, may provide a rapid and accurate assessment of the brain state of a subject. The advanced signal processing algorithms may be executed by a processor capable of integration in a portable handheld device. The portable handheld device used with a reduced electrode set allows for a rapid, on-site neurological evaluation, and determining an appropriate course of treatment at the early stage of an injury or other acute brain disorder requiring immediate medical attention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of assessing brain state of a subject comprising the steps of:
   acquiring electrical signals from the brain using at least one electrode channel;
   extracting quantitative features from the acquired signals;
   classifying the extracted features into one or more brain states; and
   computing a probabilistic index indicating the accuracy of the classification.

2. The method of claim 1, wherein multiple probabilistic indices corresponding to different classification tasks are computed.

3. The method of claim 2, wherein the multiple probabilistic indices are reported as a multidimensional vector.

4. The method of claim 2, wherein the step of classifying the extracted features is performed using a reference database.

5. The method of claim 4, wherein the reference database comprises of electrical brain activity signals/data from a plurality of individuals in the presence or absence of brain abnormalities.

6. The method of claim 4, further comprising the step of deriving an index map by graphically plotting the probabilistic indices generated from the brain electrical activity data in the reference database.

7. The method of claim 6, further comprising the step of modifying a decision boundary in the index map by incorporating new data into the map.

8. The method of claim 7, wherein the multidimensional vector is plotted on the index map.

9. The method of claim 1, wherein the index computed is a Brain Abnormality Index (BAI) indicating the accuracy of a normal vs. abnormal classification.

10. The method of claim 1, wherein the index computed is a Brain Focality Index (BFI) indicating the accuracy of a focal vs. diffused classification.

11. The method of claim 1, wherein the electrical signals from the brain comprises spontaneous electrical activity.

12. The method of claim 1, wherein the electrical signals from the brain comprises evoked potentials.

13. The method of claim 1, wherein the electrical signals from the brain comprises spontaneous electrical activity and evoked potentials.

14. The method of claim 1, wherein the step of feature extraction is performed using diffusion geometric analysis.

15. The method of claim 1, wherein the step of feature extraction is performed using wavelet packet transformation.

16. The method of claim 1, wherein the step of feature extraction is performed using Fast Fourier Transformation.

17. The method of claim 1, wherein the classification is performed using a binary classifier.

18. The method of claim 17, wherein the classifier is a linear discriminant function classifier.

19. The method of claim 18, wherein the probabilistic index is computed from the discriminant classification score.

20. The method of claim 19, further comprising the step of plotting Receiver Operating Characteristic (ROC) curves.

21. The method of claim 1, wherein the assessment of brain state is performed using a portable, handheld device.

22. An apparatus for assessing the brain state of a subject, comprising:
   a headset comprising at least one electrode for acquiring brain electrical signals;
   a base unit; wherein
      the base unit comprises a processor configured to utilize one or more operating instructions stored in a memory to perform feature extraction from the brain electrical signals, classify the extracted signal features into one or more brain states, and compute probabilistic indices indicating the accuracy of the classification.

23. The apparatus of claim 22, wherein the processor is configured to output an objective assessment of the brain state of the subject.

24. The apparatus of claim 23, wherein the processor is configured to output the probabilistic indices.

25. The apparatus of claim 22, further comprising a display wherein a result of one or more operations performed by the processor is displayed.

26. The apparatus of claim 25, wherein the probabilistic indices are reported on the display as horizontal index bars.

27. The apparatus of claim 25, wherein the probabilistic indices are reported on the display as a multidimensional vector.

28. The apparatus of claim 27, wherein an index map generated from the probabilistic indices is reported on the display.

29. The apparatus of claim 28, wherein the multidimensional vector is superimposed on the index map.

30. The apparatus of claim 28, wherein the index map is stored in the memory.

31. The apparatus of claim 28, wherein the index map is partitioned into multiple regions corresponding to different brain states.

32. The apparatus of claim 30, wherein the processor is configured to accept instructions from a user to modify a decision boundary corresponding to a brain state on the index map.

* * * * *